United States Patent [19]

Minaskanian et al.

[11] Patent Number: 4,755,535

[45] Date of Patent: Jul. 5, 1988

[54] COMPOSITIONS COMPRISING 1-SUBSTITUTED AZACYCLOALKENES

[75] Inventors: Gevork Minaskanian, Irvine; James V. Peck, Costa Mesa, both of Calif.

[73] Assignee: Nelson Research & Development Co., Irvine, Calif.

[21] Appl. No.: 855,497

[22] Filed: Apr. 23, 1986

[51] Int. Cl.$^4$ .................. C07D 223/10; A61K 31/55
[52] U.S. Cl. .................. 514/947; 548/521; 548/546; 514/946; 514/919; 514/448; 514/441; 514/212; 514/326; 514/315; 502/167; 71/88; 71/94; 71/95; 8/564; 540/524; 540/525; 540/529; 540/530; 540/531; 546/193; 546/194; 546/281; 546/265; 546/262; 546/290
[58] Field of Search .................. 502/167; 514/946, 947, 514/919, 212, 316, 326, 315, 441, 448; 540/524, 525, 529, 530, 531; 71/88, 94, 95; 546/290, 281, 265, 262, 194, 193; 8/564; 548/546, 521

[56] References Cited

U.S. PATENT DOCUMENTS

| | | | |
|---|---|---|---|
| 4,405,616 | 9/1983 | Rajadhyaksha | 514/947 |
| 4,415,563 | 11/1983 | Rajadhyaksha | 514/947 |
| 4,423,040 | 12/1983 | Rajadhyaksha | 514/947 |
| 4,424,210 | 1/1984 | Rajadhyaksha | 514/947 |
| 4,444,762 | 4/1984 | Rajadhyaksha | 514/947 |
| 4,525,199 | 6/1985 | Rajadhyaksha | 514/947 |
| 4,557,934 | 12/1985 | Cooper | 514/947 |
| 4,562,075 | 12/1985 | Rajadhyaksha | 514/945 |

FOREIGN PATENT DOCUMENTS

| | | |
|---|---|---|
| 947764 | 5/1974 | Canada. |
| 1343426 | 1/1974 | United Kingdom. |
| 2078725A | 1/1982 | United Kingdom. |

OTHER PUBLICATIONS

Rothe and Toth, "Chem. Bernchte" Band 99 No. (12), pp. 3820-3829 (1966).

English Abstract of Spanish Patent Application ES 549,688, Mar. 16, 1986.

*Primary Examiner*—Robert T. Bond
*Attorney, Agent, or Firm*—June M. Bostich

[57] ABSTRACT

This invention provides compositions comprising a physiologically-active agent and an azacycloalkene having at least one double bond in the ring and of the general formula

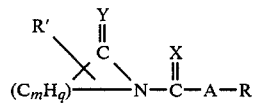

wherein X and Y, each, may represent sulfur, oxygen or two hydrogen atoms, A is a straight or branched chain, divalent aliphatic radical having from 0 to 2 double bonds; R' is selected from the group consisting of H, a lower alkyl group having 1-4 carbon atoms, phenyl, lower alkyl or halogen substituted phenyl, acetamido, halogen, piperidinyl, lower alkyl or halogen substituted piperidinyl, carbalkoxy, carboxamide, and alkylformyl; m is 3-7; q is 2m-2x, wherein x equals the number of double bonds in the lactam ring and may be 1, 2 or 3; and R is —CH$_3$,

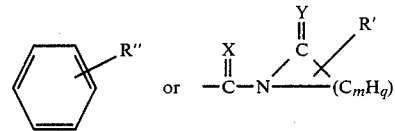

wherein R" is H or halogen in an amount effective to enhance the penetration of the physiologically-active agent through the skin or other membrane of the body of an animal.

39 Claims, No Drawings

COMPOSITIONS COMPRISING 1-SUBSTITUTED AZACYCLOALKENES

BACKGROUND OF THE INVENTION

1. Field of the Invention

This invention relates to compositions comprising a physiologically-active agent and a 1-alkyl or substituted alkyl azacycloalkene which may be substituted with a sulfur or oxygen atom pendant from one of the alpha carbon atoms of the ring and/or the alpha carbon atom of the 1-substituent in an amount effective to enhance the penetration of the physiologically-active agent through the skin or other membrane of the body of an animal.

2. Background of the Art

Many physiologically active agents are best applied topically to obtain desirable results. Topical application, as contrasted to systemic application, can avoid metabolic degradation of the agents, largely avoids side effects of the agents and permits high local concentrations of the agents.

The greatest problem in applying physiologically active agents topically is that the skin is such an effective barrier to penetration. The epidermis of the skin has an exterior layer of dead cells called the stratum corneum which is tightly compacted and oily and which provides an effective barrier against gaseous, solid or liquid chemical agents, whether used alone or in water or oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use to treat such conditions as inflammation, acne, psoriasis, herpes simplex, eczema, infections due to fungus, virus or other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellants and the like.

Physiologically active agents may be applied to locally affected parts of the body through the vehicle system described herein. Vehicles such as USP cold cream, ethanol and various ointments, oils, solvents, and emulsions have been used heretofore to apply physiologically active ingredients locally. Most such vehicles are not effective to carry significant amounts of physiologically active agents through the skin. One such vehicle is dimethyl sulfoxide.

The 1-lower alkyl substituted azacyclopentan-2-ones having 1–4 carbon atoms in the alkyl group are known to moderately enhance percutaneous absorption of chemicals, e.g. drugs. It was earlier recognized that it would be desirable to obtain the same or higher level of percutaneous absorption with substantially lower concentrations of the penetration-enhancing compound. Therefore, a new class of N-substituted azacycloalkan-2-ones were invented having the desired properties. This new class of penetration-enhancing agents are described in U.S Pat. Nos. 3,989,815; 3,989,816; 3,991,203; 4,122,170; 4,316,893; 4,405,616; 4,415,563; 4,423,040; 4,424,210; and 4,444,762, which are hereby incorporated by reference.

It is an object of this invention to provide new penetration-enhancing agents having the desirable property of enhancing the percutaneous absorption of physiologically-active agents at concentrations lower than the 1-lower alkyl substituted azacyclopentan-2-ones.

It is also an object of this invention to provide penetration-enhancing agents that are equivalent to the aforesaid new class penetration-enhancing agents described in the above U.S. patents.

Other objects and advantages of the instant invention will be apparent from a careful reading of the specification below.

In this description, the term "animal" includes human beings as well as other forms of animal life, and especially domesticated animals and pets.

SUMMARY OF THE INVENTION

This invention relates to compositions for carrying physiologically active agents through body membranes such as skin and for retaining these agents in body tissues. More specifically, the invention relates to compositions useful in topically administering a physiologically active agent to a human or animal comprising the agent and an effective, non-toxic amount of an azacycloalkene having at least one double bond in the ring and of the general formula.

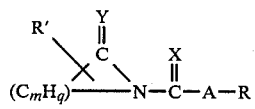

wherein X and Y, each, may represent sulfur, oxygen or two hydrogen atoms, A is a branched or a straight chain, divalent aliphatic radical having from 0 to 2 double bonds; R' is selected from the group consisting of H, a lower alkyl group having 1–4 carbon atoms, phenyl, lower alkyl or halogen substituted phenyl, acetamido, halogen, piperidinyl, lower alkyl or halogen substituted piperidinyl, carbalkoxy, carboxamide, and alkylformyl; m is 3–7; q is 2m–2x, wherein x equals the number of double bonds in the lactam ring and may be 1, 2 or 3, and R is —CH$_3$,

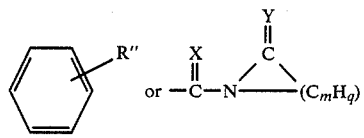

wherein R" is H or halogen.

Preferably R is —CH$_3$, R' is H, at least one of X or Y is oxygen or sulfur and A is a divalent radical represented by the general formula

wherein n is 0 to 17.

In a more preferred embodiment of the present invention Y is oxygen, X represents two hydrogen atoms, R is —CH$_3$, R' is H, x is 1 and m equals 5. Even more preferably n is 4–16, e.g. 10.

It has been found that the physiologically active agents are carried through body membranes by the above penetration-enhancing agents and are retained in body tissue.

The invention further relates to the penetration-enhancing agents themselves and their method of making.

DETAILED DESCRIPTION OF THE INVENTION

The 1-substituted azacycloalkenes useful as penetration-enhancing additives in the compositions of the instant invention may be made by the methods described below. Typical examples of compounds represented by the above general formula include:

1-Methylazacyclohept-4,6-diene-2-one
1-Ethylazacyclohept-3-ene-2-one
3-Methyl-1-(phenylmethyl)-azacyclohept-3-ene-2-one
1-Dodecylazacyclohept-3-ene-2-one
1-Dodecylazacyclohept-4-ene-2-one
1-Dodecylazacyclohept-3,5-dien-2-one
1-Methyl-4-phenyl-azacyclohept-4,6,-diene-2-one
1-Methyl-5-phenyl-azacyclohept-4,6-diene-2-one
1-Methyl-6-phenyl-azacyclohept-4,6-diene-2-one
4-N,N-Diethylcarbamyl-1-methyl-azacyclohept-4,6-diene-2-one
6-N,N-Diethylcarbamyl-1-methyl-azacyclohept-4,6-diene-2-one
6-Chloro-1-methyl-azacyclohept-4,6-diene-2-one
1-Methyl-3-(1-piperidinyl)-azacyclohept-3-ene-2-one
3-Methoxy-1-methyl-azacyclohept-3-ene-2-one
4-Methoxy-1-methyl-azacyclohept-4,6-diene-2-one
1-Acetylazacyclohept-3-ene-2-one
1-Acetylazacyclohept-4-ene-2-one
4-Acetyl-1-methyl-azacyclohept-4,6-diene-2-one
3-Methyl-1-(phenylmethyl)-azacyclohept-3-ene-2-one Many of the compounds represented by the above general formula are well known. In addition, the Examples, below, illustrate methods for preparing many of the compounds represented by the above general formula. Finally, any of the above compounds wherein X or Y is sulfur may be made by reacting the corresponding oxygen compound with phosphorus pentasulfide.

The amount of azacycloalkene which may be used in the present invention is an effective, non-toxic amount for enhancing percutaneous absorption. Generally, this amount ranges between about 0.01 to about 5 and preferably about 0.1 to 2 percent by weight of the composition.

The subject compositions may find use with many physiologically active agents which are soluble in the vehicles disclosed.

Fungistatic and fungicidal agents such as, for example, thiabendazole, chloroxine, amphotericin B, candicidin, fungimycin, nystatin, chlordantoin, clotrimazole, miconazole nitrate, pyrrolnitrin, salicylic acid, fezatione, tolnaftate, triacetin and zinc and sodium pyrithione may be dissolved in the penetration-enhancing agents described herein and topically applied to affected areas of the skin. For example, fungistatic or fungicidal agents so applied are carried through the stratum corneum, and thereby successfully treat fungus-caused skin problems. These agents, thus applied, not only penetrate more quickly than when applied in the vehicles of the prior art, but additionally enter the animal tissue in high concentrations and are retained for substantially longer time periods whereby a far more successful treatment is effected.

For example, the subject compositions may also be employed in the treatment of fungus infections on the skin caused by candida and dermatophytes which cause athletes foot or ringworm, by dissolving thiabendazole or similar antifungal agents in one of the above-described penetration-enhancing agents and applying it to the affected area.

The subject compositions are also useful in treating skin problems, for example, herpes simplex, which may be treated by a solution of iododeoxyuridine dissolved in one of the penetration-enhancing agents or such problems as warts which may be treated with agents such as podophylline dissolved in one of the penetration-enhancing agents. Skin problems such as psoriasis may be treated by topical application of a solution of a conventional topical steroid in one of the penetration-enhancing agents or by treatment with theophylline or antagonists of $\beta$-adrenergic blockers such as isoproterenol in one of the penetration-enhancing agents. Scalp conditions such as alopecia areata may be treated more effectively by applying steroids such as triamcinolone acetonide dissolved in one of the penetration-enhancing agents of this invention directly to the scalp.

The subject compositions are also useful for treating mild eczema, for example, by applying a solution of fluocinolone acetonide or its derivatives; hydrocortisone, triamcinolone acetonide, indomethacin, or phenylbutazone dissolved in one of the penetration-enhancing agents to the affected area.

Examples of other physiologically active steroids which may be used with the vehicles include corticosteroids such as, for example, cortisone, cortodoxone, flucetonide, fluorocortisone, difluorsone diacetate, flurandrenolone acetonide, medrysone, amcinafel, amcinafide, betamethasone and its esters, chloroprednisone, clocortelone, descinolone, desonide, dexamethasone, dichlorisone, defluprednate, flucloronide, flumethasone, flunisolide, fluocinonide, flucortolone, fluoromethalone, fluperolone, fluprednisolone, meprednisone, methylmeprednisolone, paramethasone, prednisolone and prednisone.

The subject compositions are also useful in antibacterial chemotherapy, e.g. in the treatment of skin conditions involving pathogenic bacteria. Typical antibacterial agents which may be used in this invention include sulfonamides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, etc.

The subject compositions are also useful in protecting ultra-sensitive skin or even normally sensitive skin from damage or discomfort due to sunburn. Thus, dermatitis actinica may be avoided by application of a sunscreen, such as para-aminobenzoic acid or its well-known derivatives dissolved in one of the above-described penetration-enhancing agents, to skin surfaces that are to be exposed to the sun; and the protective para-aminobenzoic acid or its derivatives will be carried into the stratum corneum more successfully and will therefore be retained even when exposed to water or washing for a substantially longer period of time than when applied to the skin in conventional vehicles. This invention is particularly useful for ordinary suntan lotions used in activities involving swimming because the ultraviolet screening ingredients in the carriers of the prior art are washed off the skin when it is immersed in water.

The subject compositions may also find use in treating scar tissue by applying agents which soften collagen, such as aminopropionitrile or penicillamine dissolved in one of the penetration-enhancing agents of this invention topically to the scar tissue.

Agents normally applied as eye drops, ear drops, or nose drops are more effective when dissolved in the penetration-enhancing agents of this invention.

Agents used in diagnosis may be used more effectively when applied dissolved in one of the penetration-enhancing agents of this invention. Patch tests to diagnose allergies may be effected promptly without scratching the skin or covering the area subjected to an allergen when the allergens are applied in one of the penetration-enhancing agents of this invention.

The subject compositions are also useful for topical application of cosmetic or esthetic agents. For example, compounds such as melanin-stimulating hormone (MSH) or dihydroxyacetone and the like are more effectively applied to skin to stimulate a suntan when they are dissolved in one of the penetration-enhancing agents of this invention. The agent is carried into the skin more quickly and in greater quantity when applied in accordance with this invention. Hair dyes also penetrate more completely and effectively when dissolved in one of the penetration-enhancing agents of this invention.

The effectiveness of such topically applied materials as insect repellants or fragrances, such as perfumes and colognes, can be prolonged when such agents are applied dissolved in one of the penetration-enhancing agents of this invention.

It is to be emphasized that the foregoing are simply examples of physiologically active agents including therapeutic and cosmetic agents having known effects for known conditions, which may be used more effectively for their known properties in accordance with this invention.

In addition, the penetration-enhancing agents of the present invention may also be used to produce therapeutic effects which were not previously known. That is, by use of the penetration-enhancing agents described herein, therapeutic effects heretofore not known can be achieved.

As an example of the foregoing, griseofulvin is known as the treatment of choice for fungus infections of the skin and nails. Heretofore, the manner of delivery of griseofulvin has been oral. However, it has long been known that oral treatment is not preferred because of side effects resulting from exposure of the entire body to griseofulvin and the fact that only the outer layers of affected skin need to be treated. Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be delivered topically which would cause sufficient retention of griseofulvin in the skin to be useful therapeutically.

However, it has now been discovered that griseofulvin, in a range of therapeutic concentrations between about 0.1% and about 10% may be used effectively topically if combined with one of the penetration-enhancing agents described herein.

As a further example, acne is the name commonly applied to any inflammatory disease of the sebaceous glands; also acne vulgaris. The microorganism typically responsible for the acne infection is Corynebacterium acnes. Various therapeutic methods for treating acne have been attempted including topical antibacterials, e.g. hexachlorophene, and systemic antibiotics such as tetracycline. While the systemic antibiotic treatments are known to be partially effective, the topical treatments are generally not effective.

It has long been known that systemic treatment of acne is not preferred because of side effects resulting from exposure of the entire body to antibiotics and the fact that only the affected skin need be treated. However, despite a long-felt need for a topical treatment for acne, antibiotics generally have been used only systemically to treat acne because there was not heretofore known an antibacterial formulation which could be used topically which would be effective therapeutically in the treatment of acne. However, it has now been discovered that antibiotics, especially those of the lincomycin and erythromycin families of antibiotics, may be used in the treatment of acne topically if combined with one of the penetration-enhancing agents described herein.

The antibiotics composition so applied is carried into and through the epidermis and deeper layers of the skin as well as into follicles and comedones (sebum-plugged follicles which contain C. acnes) in therapeutically effective amounts and thereby successfully may be used to temporarily eliminate the signs and symptoms of acne.

The term "physiologically active agent" is used herein to refer to a broad class of useful chemical and therapeutic agents including physiologically active steroids, antibiotics, antifungal agents, antibacterial agents, antineoplastic agents, allergens, antihistaminic agents, anti-inflammatory agents, ultraviolet screening agents, diagnostic agents, perfumes, insect repellants, hair dyes, etc.

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freons, ethyl alcohol, polyvinylpyrrolidone, propylene glycol, fragrances, gel-producing materials, mineral oil, stearyl alcohol, stearic acid, spermaceti, sorbitan monooleate, "Polysorbates", "Tweens", sorbital, methyl cellulose, etc.

The amount of the composition, and thus of the physiologically active agent therein, to be administered will obviously be an effective amount for the desired result expected therefrom. This, of course, will be ascertained by the ordinary skill of the practitioner. Due to enhanced activity which is achieved, the dosage of physiologically active agent may often be decreased from that generally applicable. In accordance with the usual prudent formulating practices, a dosage near the lower end of the useful range of the particular physiologically active agent may be employed initially and the dosage increased as indicated from the observed response, as in the routine procedure of the physician.

The invention is further illustrated by the following examples which are illustrative of various aspects of the invention, and are not intended as limiting the scope of the invention as defined by the appended claims.

EXAMPLE 1

Preparation of 1-Dodecylazacyclohept-3-ene-2-one

A. Preparation of 3-Bromo-1-dodecylazacycloheptan-2-one

To a cold solution of 107 g (0.38 mol) of 1-dodecylazacycloheptan-2-one, in CHCl$_3$ was added 159.7 g (0.77 mol) of PCl$_5$, keeping the temperature between 1°–4° C. After 2 hours, a solution of 123.3 g (0.77 mol) of bromine in CHCl$_3$ was added, and the mixture was stirred for 18 hours at room temperature. After removing the solvent and excess bromine by vacuum distillation, the residue was dissolved in CH$_2$Cl$_2$, washed with sat. Na$_2$S$_2$O$_5$, dried over MgSO$_4$, and concentrated in vacuo to give a crude oil. Purification by flash chromatography (silica gel; 1:1 ether/petroleum ether V/V) gave pure product.

B. Preparation of 1-Dodecylazacyclohept-3-ene-2-one

A solution of 10.0 g (28 mmol) of 3-bromo-1-dodecylazacycloheptan-2-one and 5.1 g (47 mmol) of 2,6-lutidine was refluxed for 3 hours, then cooled to room temperature. 100 ml of toluene was added, the mixture was filtered, and the filtrate was concentrated in vacuo to yield a crude oil. Purification by flash chromatography (silica gel; 7:3 petroleum ether/ether V/V) gave the product as a colorless oil, R$_f$=0.38; Kuglerohr distilled at 165°–170° C./0.2 mm Hg.

EXAMPLE 2

Preparation of 1-Dodecylazacyclohept-4-ene-2-one

A solution of 10.0 g (28 mmol) of 3-bromo-1-dodecylazacycloheptan-2-one (Example 1-A) and 5.1 g 47 mmol) of 2,6-lutidine was refluxed for 3 hours. The reaction was cooled to room temperature, 100 ml of toluene was added, and the mixture was filtered. The filtrate was concentrated in vacuo and the residue subjected to flash chromatography (silica gel; 7:3 petroleum ether/EtOAc V/V) to yield the product as a white solid, R$_f$=0.5; Kuglerohr distilled at 155°–160° C./0.2 mm Hg.

EXAMPLE 3

An Improved Preparation of 1-Dodecylazacyclohept-3-ene-2-one

A. Preparation of 3,3-Dibromoazacycloheptan-2-one

To a cold solution of 45.2 g (0.4 mol) of caprolactam in CHCl$_3$ was added 166.0 g (0.8 mol) of PCl$_5$, keeping the temperature less than 5° C. The mixture was brought to room temperature, 2.0 g of ZnCl$_2$ was added, and finally 128 g (0.8 mol) of bromine was added dropwise. After stirring the mixture for 5 hours at room temperature, the solvent and excess bromine was removed by vacuum distillation. The residue was poured into ice water and extracted with CH$_2$Cl$_2$. The combined organic extracts were washed with sat. Na$_2$S$_2$O$_5$, dried over MgSO$_4$, and concentrated in vacuo to give a crude solid. Washing the solid with CH$_2$Cl$_2$/toluene yielded the product as a white powder; mp 156°–159° C.

B. Preparation of 3-Bromo azacycloheptan-2-one

A solution of 16 g (59 mmol) of 3,3-dibromoazacycloheptan-2-one, 150 ml of glacial acetic acid, 5.5 g (65 mmol) of sodium acetate, and 0.5 g of palladium on carbon (10%) was placed in a hydrogenator bottle and reduced under hydrogen at 30 psi. The mixture was filtered, and the filtrate distilled under vacuum to remove the acetic acid. The residue was neutralized with sat. Na$_2$CO$_3$, extracted into CH$_2$Cl$_2$, dried over MgSO$_4$, and concentrated to yield 10.8 g (95%) of the product as an off-white solid; mp 109°–111° C.; NMR (CDCl$_3$) 7.2 (1 H,m), 4.6 (1 H,m), 3.4 (2 H,m), 2.1 (4 H,m), 1.7 (2 H,m).

C. Preparation of Azacyclohept-3-ene-2-one and Azacyclohept-4-ene-2-one

A solution of 15 g (0.08 mol) of 3-bromoazacycloheptan-2-one and 14 g (0.13 mol) of 2,6-lutidine was refluxed for 3 hours. The mixture was filtered, the filtrate was concentrated in vacuo, and the residue was distilled under vacuum (80° C./0.02 mm Hg) to yield 6.13 g (70%) of a colorless oil which was identified by GC and NMR as a mixture of azacyclohept-3-ene-2-one and azacyclohept-4-ene-2-one. The mixture was used without purification for the next synthetic step.

D. Preparation of 1-Dodecylazacyclohept-3-ene-2-one

A solution of 11.4 g (0.102 mol) of a mixture of azacyclohept-3-ene-2-one and azacyclohept-4-ene-2-one in THF was added dropwise to a suspension of 4.8 g (107 mmol) of sodium hydride (50% oil dispersion) in THF. The mixture was stirred at room temperature for 1 hour, 25.4 g (0.102 mol) of dodecyl bromide was added, and the solution was refluxed for 5 hours. The mixture was cooled, water was added, and the solvent was removed in vacuo. The residue was dissolved in CH$_2$Cl$_2$, washed with water, the organic phase dried over MgSO$_4$ and concentrated in vacuo to yield an oil which was Kugelrohr distilled to give 15.5 g of crude product. This material was subjected to flash chromatography (silica gel; 9:1 petroleum ether/ether V/V) to give 1-dodecylazacyclohept-3-ene-2-one, R$_f$=0.5, GC (column: 48 inch, 2% OV 101; conditions: injector, detector 320° C., program; 140° C. for 3 min, then to 190° C. in 30° C./min) GC retention time, 7.74 min.

EXAMPLE 4

Preparation of 1-Dodecylazacyclohept-4-ene-2-one (Improved Method)

A solution of 11.4 g (0.102 mol) of a mixture of azacyclohept-3-ene-2-one and azacyclohept-4-ene-2-one (Example 3-C) in THF was added dropwise to a suspension of 4.8 g (107 mmol) of sodium hydride (50% oil dispersion) in THF. The mixture was stirred at room temperature for 1 hour, 25.4 g (0.102 mol) of dodecyl bromide was added, and the solution was refluxed for 5 hours. The mixture was cooled, water was added, and the solvent was removed in vacuo. The residue was dissolved in CH$_2$Cl$_2$, washed with water, the organic phase dried over MgSO$_4$ and concentrated in vacuo to yield an oil which was Kugelrohr distilled to give 15.5 g of a crude product. This material was subjected to flash chromatography (silica gel; 9:1 petroleum ether/ether V/V) to give 1-dodecylazacyclohept-4-ene-2-one, R$_f$=0.45; GC retention time 7.4 min. GC conditions identical to Example 3-D.

EXAMPLE 5

Preparation of 1-Dodecylazacyclohept-3,5-dien-2-one

A. Preparation of 4,5-Dibromo-1-dodecylazacycloheptan-2-one

A solution of 1.14 g (7.13 mmol) of bromine in $CCl_4$ was added to a solution of 2.0 g (7.13 mmol) of 1-dodecylazacyclohept-4-ene-2-one in $CCl_4$ at 0° C. The mixture was stirred for 10 minutes, then washed with a sat. $Na_2S_2O_4$ solution. The organic layer was separated, dried over $MgSO_4$, and concentrated to yield 3.4 g of crude 4,5-dibromo-1-dodecylazacycloheptan-2-one. This product was used for the next synthetic step without purification.

B. Preparation of 1-Dodecylazacyclohept-3,5-dien-2-one

A solution of 3.4 g (7.72 mmol) of 4,5-dibromo-1-dodecylazacycloheptan-2-one in 5.79 g (0.054 mol) of 2,6-lutidine was refluxed for 3 hours. After standing at room temperature for 20 hours, toluene was added, and the solution was filtered. The filtrate was concentrated in vacuo and distilled to give 3.8 g of a crude oil which was subjected to flash chromatography (silica gel; 3:1 petroleum ether/ether V/V) to yield pure product.

This compound, as well as homologues thereof, wherein the 1-substituent comprises at least three carbon atoms, e.g. from seven to seventeen carbon atoms, are believed to be novel, and may be prepared by analogous procedures.

EXAMPLE 6

The compounds of Examples 1 and 2 were tested as penetration enhancing agents according to the below procedure:

Skin from female hairless mice, 4–6 weeks old, was removed from the animal and placed over penetration wells with normal saline bathing the corium. A plastic cylinder 1.4 cm in diameter was glued onto each piece on the epidermal side. 0.1% triamcinolone acetonide $^3H$ was applied (0.01 cc) to the epidermal surface within the 1.4 cm diameter cylinder. The skin was incubated at room temperature and ambient humidity.

At 6 hours and 24 hours, 2 cc were removed from the 10 cc reservoir of normal saline bathing the corium. The 2 cc of normal saline removed were replaced after the 6 hour sample with 2 cc of normal saline.

The 2 cc aliquots were put into scintillation fluid and the radioactivity determined in a scintillation counter. The amount penetrating was calculated as percent of dose applied.

In every experiment the $^3H$ triamcinolone acetonide was dissolved in ethanol and the penetration-enhancing agent to be tested was added to the desired concentration.

The controls were ethanol, alone, and 1-n-dodecylazacycloheptan-2-one, a compound described in the U.S. patents, noted above, as having superior penetration-enhancing properties. Five separate tests for each compound and the controls were made and the results averaged.

The results, as reported in the Table below, show that the compounds of Examples 1 and 2 have penetration-enhancing properties at least equivalent to 1-n-dodecylcycloheptan-2-one.

TABLE

| Penetration-Enhancing Agent | Percent Penetration | |
|---|---|---|
| | 6 hr. | 24 hr. |
| 1-Dodecylazacyclohept-4-ene-2-one | 15.4 | 60.0 |
| 1-Dodecylazacyclohept-3-ene-2-one | 12.6 | 62.5 |
| 1-n-Dodecylcycloheptan-2-one | 10.6 | 61.3 |
| Ethanol (only) | 0.4 | 3.8 |

EXAMPLE 7

The following formulation is prepared:

| | Solution (%) |
|---|---|
| Griseofulvin | 1 |
| 1-Dodecylazacyclohept-3-ene-2-one | 1 |
| Isopropyl myristate | 5 |
| Fragrance | 0.1 |
| Ethanol | 92.9 |

This formulation is effective in the treatment of fungus infections.

EXAMPLE 8

An aerosol form of the formulation of Example 7 is prepared by preparing the following mixture:

| | |
|---|---|
| Formulation | 25% |
| Freon[1] | 75% |

[1]Freon is 75/25 Freon 114/12.

EXAMPLE 9

The following cream formulation is prepared:

| | % |
|---|---|
| Clindamycin base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 1-Dodecylazacyclohept-3-ene-2-one | 0.5 |
| Sorbitol solution, U.S.P. | 5.5 |
| Sodium citrate | 0.5 |
| Chemoderm #844 Fragrance | 0.2 |
| Purified water | 68.4 |

This formulation is effective in the treatment of acne.

EXAMPLE 10

The following solution formulations are prepared:

| | A (%) | B (%) |
|---|---|---|
| Clindamycin base | — | 1.0 |
| Clindamycin phosphate acid | 1.3 | — |
| Sodium hydroxide | 0.077 | — |
| 1.0 M Hydrochloric acid | — | 2.27 |
| Disodium edetate.2H$_2$O | 0.003 | 0.003 |
| Fragrances | 0.5 | 0.5 |
| 1-Dodecylazacyclohept-3-ene-2-one | 1.0 | 1.0 |
| Purified water | 20.0 | 17.73 |
| Isopropanol | 77.12 | 77.497 |

These solutions are effective for the treatment of acne in humans.

EXAMPLE 11

The following solution formulation is prepared:

|  | % |
|---|---|
| Neomycin sulfate | 0.5 |
| Lidocaine | 0.5 |
| Hydrocortisone | 0.25 |
| 1-Dodecylazacyclohept-3-ene-2-one | 0.5 |
| Propylene glycol | 98.25 |

This solution is effective for the treatment of otitis in domestic animals.

EXAMPLE 12

The following sunscreen emulsion is prepared:

|  | % |
|---|---|
| p-Aminobenzoic acid | 2.0 |
| Benzyl alcohol | 0.5 |
| 1-Dodecylazacyclohept-3-ene-2-one | 1.0 |
| Polyethylene glycol 500-MS | 10.0 |
| Isopropyl lanolate | 3.0 |
| Lantrol | 1.0 |
| Acetylated lanolin | 0.5 |
| Isopropyl myristate | 5.0 |
| Light mineral oil | 8.0 |
| Cetyl alcohol | 1.0 |
| Veegum | 1.0 |
| Propylene glycol | 3.0 |
| Purified water | 64.0 |

EXAMPLE 13

The following antineoplastic solution is prepared:

|  | % |
|---|---|
| 5-Fluorouracil | 5.0 |
| 1-Dodecylazacyclohept-3-ene-2-one | 0.1 |
| Polyethylene glycol | 5.0 |
| Purified water | 89.9 |

EXAMPLE 14

The following insect repellant atomizing spray is prepared:

|  | % |
|---|---|
| Diethyltoluamide | 0.1 |
| 1-Dodecylazacyclohept-3-ene-2-one | 0.1 |
| Ethanol | 99.8 |

EXAMPLE 15

The following lotion formulation may be prepared containing about 0.001 to 1 percent, with preferably 0.1 percent fluocinolone acetonide:

|  | % |
|---|---|
| Fluocinolone acetonide | 0.001–1 |
| Cetyl alcohol | 15.0 |
| Propylene glycol | 10.0 |
| Sodium lauryl sulfate | 15.0 |
| 1-Dodecylazacyclohept-3-ene-2-one | 1.0 |
| Water (to make 100%) |  |

The steroid is dissolved in the vehicle and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of the steroid into the inflamed tissue is enhanced and a therapeutic level is achieved more rapidly and sustained for longer duration than when the steroid is applied in conventional formulations.

EXAMPLE 16

Examples 7–15 are repeated except that 1-dodecylazacyclohept-3-ene-2-one is replaced with 1-dodecylazacyclohept-4-ene-2-one. Comparable results are obtained.

While particular embodiments of the invention have been described it will be understood of course that the invention is not limited thereto since many obvious modifications can be made and it is intended to include within this invention any such modifications as will fall within the scope of the appended claims.

Having now described the invention, we claim:

1. A composition comprising an effective amount of a physiologically active agent and a non-toxic, effective penetrating amount of an azacycloalkene having at least one double bond in the ring and of the general formula $$(C_mH_q)\underset{\underset{}{}}{\overset{R'}{\underset{}{\diagdown}}}\overset{Y}{\underset{\|}{C}}\diagup\underset{}{}\overset{X}{\underset{\|}{}}\!\!\!\!\!\!\text{N}-\text{C}-\text{A}-\text{R}$$

wherein X and Y, each, may represent sulfur, oxygen or two hydrogen atoms, A is a branched or straight chain, divalent aliphatic radical having from 0 to 2 double bonds; R' is selected from the group consisting of H, a lower alkyl group having 1–4 carbon atoms, phenyl, lower alkyl or halogen substituted phenyl, acetamido, halogen, piperidinyl, lower alkyl or halogen substituted piperidinyl, carbalkoxy, carboxamide, and alkylformyl; m is 3–7; q is 2m–2x, wherein x equals the number of double bonds in the lactam ring and may be 1, 2 or 3, and R is CH₃, $$\text{phenyl}-R'' \quad \text{or} \quad -\overset{X}{\underset{\|}{C}}-\text{N}\diagup\overset{Y}{\underset{\|}{C}}\diagdown R' \diagdown (C_mH_q)$$

wherein R'' is H or halogen.

2. The composition of claim 1 wherein the physiologically active agent is an antibacterial agent.

3. The composition of claim 2, wherein the antibacterial agent is an antibiotic.

4. The composition of claim 3 wherein the antibiotic is selected from the group consisting of lincomycin, clindamycin, erythromycin and pharmaceutically useful salts thereof.

5. The composition of claim 1 wherein the physiologically active agent is a physiologically active steroid.

6. The composition of claim 1 wherein the physiologically active agent is an antifungal agent.

7. The composition of claim 1 wherein the physiologically active agent is iododeoxyuridine.

8. The composition of claim 1 wherein the physiologically active agent is 5-fluorouracil.

9. A composition useful for topically administering a physiologically active agent to a human or animal comprising an effective amount of a physiologically active agent and a non-toxic, effective penetrating amount of an azacycloalkene having at least one double bond in the ring and of the general formula

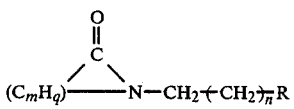

wherein m is 5; q is 10-2x, wherein x equals the number of double bonds in the lactam ring and may be 1 or 2; n is 4-16 and R is —CH$_3$.

10. The composition of claim 9 wherein the physiologically active agent is an antibacterial agent.

11. The composition of claim 10 wherein the antibacterial agent is an antibiotic.

12. The composition of claim 11 wherein the antibiotic is selected from the group consisting of lincomycin, clindamycin, erythromycin and pharmaceutically useful salts thereof.

13. The composition of claim 9 wherein the physiologically active agent is a physiologically active steroid.

14. The composition of claim 9 wherein the physiologically active agent is an antifungal agent.

15. The composition of claim 9 wherein the physiologically active agent is iododeoxyuridine.

16. The composition of claim 9 wherein the physiologically active agent is 5-fluorouracil.

17. The composition of claim 9 wherein n is 10 and x is 1.

18. The composition of claim 17 wherein n is 10 and the double bond is either in the 3 or 4 position of the lactam ring.

19. A method for administering an effective amount of a physiologically active agent to and/or through the skin or other membrane of a human or animal which comprises contacting said physiologically active agent with said skin or other membrane in the presence of a non-toxic azacycloalkene having at least one double bond in the ring and of the general formula

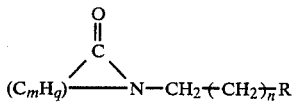

wherein X and Y, each, may represent sulfur, oxygen or two hydrogen atoms, A is a straight or branched chain, divalent aliphatic radical having from 0 to 2 double bonds; R' is selected from the group consisting of H, a lower alkyl group having 1-4 carbon atoms, phenyl, lower alkyl or halogen substituted phenyl, acetamido, halogen, piperidinyl, lower alkyl or halogen substituted piperidinyl, carbalkoxy, carboxamide, and alkylformyl; m is 3-7; q is 2m-2x, wherein x equals the number of double bonds in the lactam ring and may be 1, 2 or 3, and R is —CH$_3$,

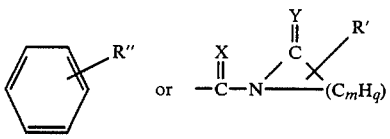

wherein R'' is H or halogen.

20. The method of claim 19 wherein the physiologically active agent is an antibacterial agent.

21. The method of claim 20, wherein the antibacterial agent is an antibiotic.

22. The method of claim 21 wherein the antibiotic is selected from the group consisting of lincomycin, clindamycin, erythromycin and pharmaceutically useful salts thereof.

23. The method of claim 19 wherein the physiologically active agent is a physiologically active steroid.

24. The method of claim 19 wherein the physiologically active agent is an antifungal agent.

25. The method of claim 19 wherein the physiologically active agent is iododeoxyuridine.

26. The method of claim 19 wherein the physiologically active agent is 5-fluorouracil.

27. A method for topically administering a physiologically active agent to a human or animal which comprises contacting said physiologically active agent with the skin or other membrane of the human or animal in the presence of a non-toxic, effective penetrating amount of an azacycloalkene having at least one double bond in the ring and of the general formula

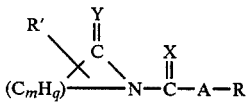

wherein m is 5; q is 10-2x, wherein x equals the number of double bonds in the lactam ring and may be 1 or 2; n is 4—16 and R is —CH$_3$.

28. The method of claim 27 wherein the physiologically active agent is an antibacterial agent.

29. The method of claim 28 wherein the antibacterial agent is an antibiotic.

30. The method of claim 29 wherein the antibiotic is selected from the group consisting of lincomycin, clindamycin, erythromycin and pharmaceutically useful salts thereof.

31. The method of claim 27 wherein the physiologically active agent is a physiologically active steroid.

32. The method of claim 27 wherein the physiologically active agent is an antifungal agent.

33. The method of claim 27 wherein the physiologically active agent is iododeoxyuridine.

34. The method of claim 27 wherein the physiologically active agent is 5-fluorouracil.

35. The method of claim 27 wherein n is 10 and x is 1.

36. The method of claim 35 wherein n is 10 and the double bond is either in the 3 or 4 position of the lactam ring.

37. 1-Alkyl substituted, azacyclohept-3,5-dien-2-ones wherein said alkyl group comprises at least three carbon atoms.

38. The compounds of claim 37 wherein said alkyl group comprises from seven to seventeen carbon atoms.

39. A compound according to claim 38 wherein said alkyl group is dodecyl.

* * * * *